United States Patent [19]
Gordon

[11] Patent Number: 4,935,002
[45] Date of Patent: Jun. 19, 1990

[54] APPARATUS AND METHOD FOR THE AUTOTRANSFUSION OF BLOOD
[75] Inventor: Lucas S. Gordon, The Woodlands, Tex.
[73] Assignee: Biodynamics, Inc., Houston, Tex.
[21] Appl. No.: 213,241
[22] Filed: Jun. 29, 1988
[51] Int. Cl.$^5$ .................. A61M 1/34; B01D 13/00
[52] U.S. Cl. .......................... 604/4; 604/5; 210/645; 210/780; 210/321.68
[58] Field of Search ................ 604/4–7, 604/252, 405, 406; 210/107, 216, 321.63, 321.67, 321.68, 645, 780–782, 789

[56] References Cited
U.S. PATENT DOCUMENTS

| 3,567,030 | 3/1971 | Loeffler | 210/321.68 |
| 4,216,770 | 8/1980 | Curtis et al. | 604/6 |
| 4,581,010 | 4/1986 | Skurkovich et al. | 604/5 |
| 4,631,050 | 9/1985 | Reed et al. | |
| 4,670,147 | 8/1985 | Schoendorfer et al. | |
| 4,675,106 | 4/1985 | Schoendorfer et al. | |
| 4,713,176 | 4/1985 | Schoendorfer et al. | |
| 4,776,964 | 10/1988 | Schoendorfer et al. | 210/321.68 |
| 4,790,942 | 12/1988 | Shmidt et al. | 210/321.68 |

FOREIGN PATENT DOCUMENTS

| 0112152 | 6/1984 | European Pat. Off. | 604/4 |
| 87302368.3 | 3/1987 | European Pat. Off. | |
| 0232884 | 8/1987 | European Pat. Off. | 604/405 |
| 0850087 | 7/1981 | U.S.S.R. | 604/4 |

OTHER PUBLICATIONS
"The Shear Rate Filtration Rate Relationship for Membranes for Plasmaphersis", by E. F. Leonard, Raven Press, New York, 1983.

Primary Examiner—Stephen C. Pellegrino
Assistant Examiner—Ralph Lewis
Attorney, Agent, or Firm—John R. Kirk, Jr.

[57] ABSTRACT

Autotransfusion apparatus and methods are disclosed for collecting, processing and returning blood to a patient during or after surgery. The processing step of the autotransfusion system comprises sequential rough filtering and filtering of the blood. Filtering is achieved within a single filter housing which includes a first ultrafiltration zone where blood fluids and anticoagulant are separated and removed from red blood cells, a washing zone where washing solution is injected into the remaining concentrated red blood cell solution and a second filtration zone where washing solution, residual blood fluids and anticoagulant are separated and removed from the washed and concentrated red blood cell solution. The filtration includes a rotating disc which creates a shear force upon the blood to prevent clotting and red blood cell build up along the face of filter membranes.

16 Claims, 4 Drawing Sheets

APPARATUS AND METHOD FOR THE AUTOTRANSFUSION OF BLOOD

BACKGROUND OF THE INVENTION

The present invention relates generally to apparatus and methods for the autotransfusion of blood. Particularly, the present invention relates to apparatus and methods for high speed processing, cleansing and reconstituting a patient's blood during operation procedures prior to returning the blood to that patient.

During and after surgery, blood is removed from the body of the patient. This blood includes healthy red and white blood cells, platelets, and blood plasma (the fluid portion of the blood) along with solid and particulate refuse resulting from the operation itself. The refuse may include the cell walls of red blood cells which have been damaged or ruptured, platelets, leukocyte aggregates, small pieces of tissue, blood clots as well as other undesirable substances. The blood removed from a patient cannot immediately be returned to the patient because of this refuse in the blood, but it is desirable to return the patient's blood rather than to supply additional blood for a number of reasons.

It is desirable to remove the blood from the patient, process it to remove the refuse and plasma, wash the remaining blood cells to remove anticoagulant, and quickly return the healthy red blood cells to the patient. If not washed, the anticoagulant builds up in the patient and causes severe problems. In the past, the blood was first filtered to remove some of the particulate refuse. The remaining whole blood was then centrifuged to separate plasma and other body fluids from red blood cells which could then be washed with a washing solution and centrifuged again to separate washing solution from the red blood cells. This process was very slow which prevented the reintroduction of a patient's own blood back to the patient during and after the surgical procedure. As a result, separate supplies of blood were needed. This raised the problems sufficient separate blood supplies free of disease-causing contaminants.

The uninterrupted process of removing a patient's blood from the patient's body, processing the blood and returning healthy red blood cells in an on-line manner is referred to herein "autotransfusion." U.S. Pat. No. 4,631,050 describes an autotransfusion device utilizing membrane filtration techniques. The device of this patent describes mixing a washing solution into the whole blood after an initial filtration to remove gross debris followed by a one-stage membrane filtration of the plasma and washing solution from the blood. No system is disclosed which separates the plasma from the whole blood prior to washing. A preferred sequence is to remove the plasma and other body fluids, wash the red blood cells and remove the washing solution. This sequence enhances fluid removal and washing of anticoagulant from the blood cells. The patent fails to disclose a means of preventing build- up of red blood cells along the membrane filter which, if not avoided, eventually results in clogging of the membrane filter.

Attempts to solve the problem of cell buildup are shown in U.S. Pat. Nos. 4,713,176, 4,670,147, and 4,675,106, which describe means of preventing build-up of red blood cells along a filter membrane due to Taylor Vortex action. They also fail to disclose a system which separates the plasma from the whole blood prior to washing and require a rotating hollow cylinder covered by a membrane filter to accomplish the filtration. No additional filtration capability is disclosed. Further, the prior art discloses apparatus and methods from the simple separation of biological cells from liquids but not a successful autotransfusion device which provides for the cleaning of red blood cells in a continuous manner. One such solution to the problem appears in European patent application No. 87302368.3, filed Mar. 19, 1987, belonging to Toray Industries, which discloses a rotating disc to impart shearing forces to blood cells during plasma phoresis. It fails, however to describe a solution to the problem unique to autotransfusion; i.e., the washing of anticoagulant from the blood cells before returning to the operative patient.

It is an object of this invention to provide an autotransfusion system using a two-stage filter which provides for a saline wash step between the filtration steps to better remove anticoagulant from blood cells.

An advantage of the system of the invention is accomplished with a filter which receives blood cells in whole blood and initially concentrates the cells by removing at least a portion of the plasma and other fluids through a first flat membrane, then washes the blood cells removing additional impurities and anticoagulant and dilutes the partially concentrated cells with a washing solution, and then removes the washing solution along with additional plasma and other fluids through a second flat membrane. The blood cells are then removed and can be returned directly to a patient.

SUMMARY OF THE INVENTION

In accordance with the primary purpose of the present invention, there is provided a high speed autotransfusion filter for rapid processing, thorough cleansing, and returning of a patient's blood during an operation. In this invention blood is removed, usually continuously, from a body cavity and first conveyed to a filter for removal of gross particulate refuse. The filtered blood is then pumped to filter of this invention where it enters an inlet port. The filter body is formed by attaching two plates along their perimeter. The plates are designed and attached to form a hollow interior region within the filter. An inlet port is placed proximate the center of a first plate. A partition is placed between the two plates to divide the interior region into a first and second filtration zone such that when filtered blood flows through the first filtration zone around the perimeter of the partition in an outward radial direction, and into the second filtration zone. A washing zone is located intermediate the filtration zones, where the blood cells contact an aqueous saline wash which serves to remove anticoagulant adhering to blood cells (white, red, and platelets) to prevent build up of anticoagulant in the patient.

A first discharge chamber is located on the first plate in an annular configuration around the inlet port. This chamber is separated from the interior region of the filter by a first membrane selected to pass the desired filtrate while leaving the cells to be collected on the membrane in the first filtration zone which move to a washing zone at the perimeter of the partition which supplies shear energy to urge concentrated blood cells along the membranes. An aqueous saline solution is injected into the wash zone to both clean the blood cells and to dilute the blood mixture. Leaving the washing zone, the mixture passes through the second filtration zone where the fluid is again removed and the blood mixture is recovered through an outlet in plate two. The second filtration zone is formed by interposing a second membrane in the interim region between the partition and the second plate. This forms a discharge zone from which filtrate is removed as the blood mixture moves across the second membrane.

DETAILED DESCRIPTION

In the specific discussion of the invention which follows, the embodiment discussed will relate to the recovery of red blood cells from the patient of an operation and returning same to such patient, it being remembered that the invention has broader application.

Figure 1:
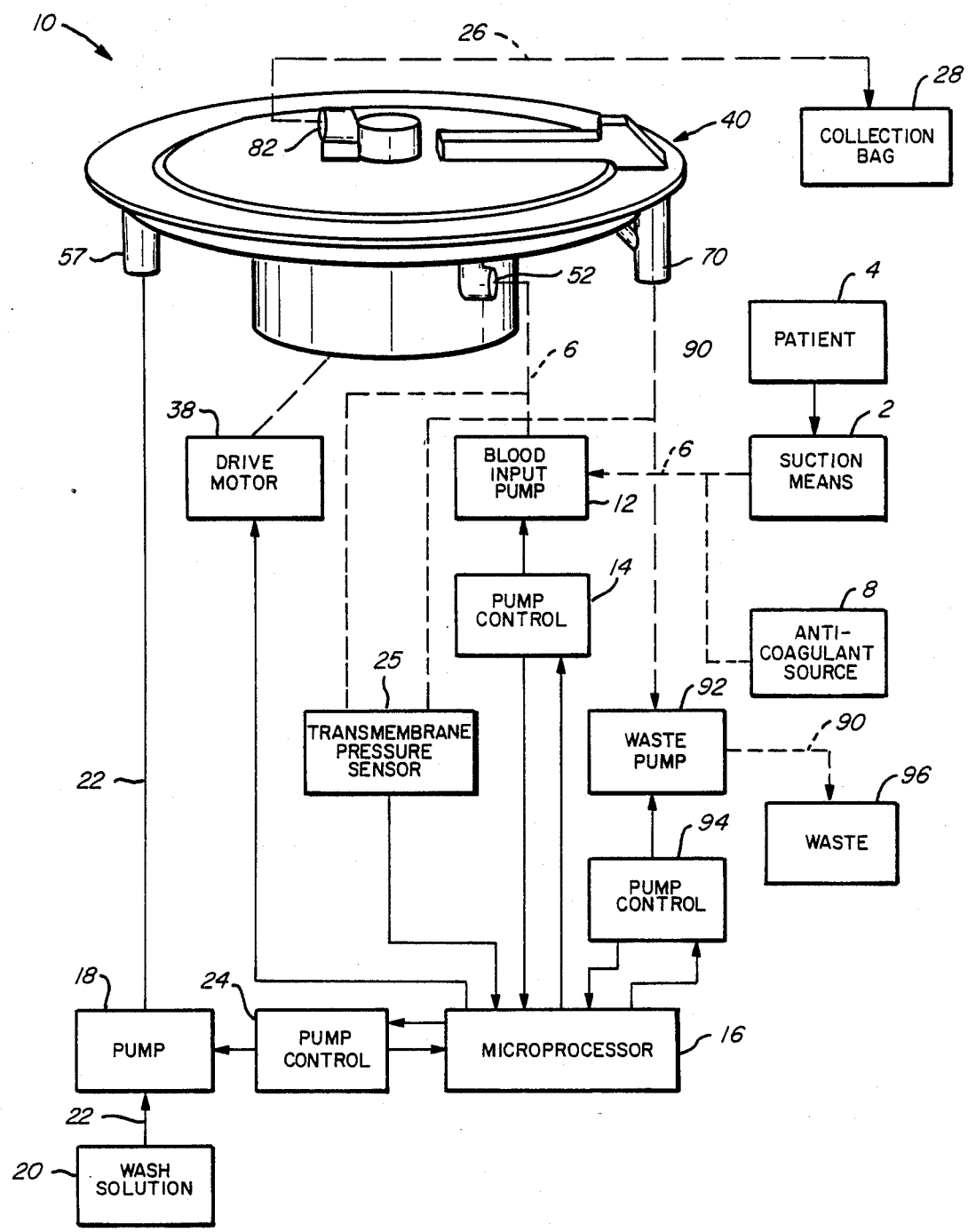
FIG. 1 is a block diagram showing schematically the parts of the preferred autotransfusion system in accordance with the invention.

Referring now to the drawings, FIG. 1, illustrates an autotransfusion system, generally designated as 10. As previously mentioned, autotransfusion system 10 is designed to process, thoroughly cleanse and return a concentrated red blood cell mixture to a patient. At a flow rate of about 200 ml./min. of blood from the patient and about 100 ml./min. back to the patient, the autotransfusion system 10 can remain on-line with the patient during and after surgery to directly support the patient. It is to be understood that throughout the description and claims, references to red blood cells is meant to include cells carried by blood, namely the white cells, red cells, and platelets unless the context of any statement clearly indicates otherwise.

As depicted in FIG. 1, autotransfusion system 10 generally comprises a suction means 2 which draws blood from patient 4, usually during an operative procedure, which blood is usually then filtered to remove gross particulate matter (not shown). The blood proceeds through conduit 6 to which is added an anticoagulant from a source 8 through blood input pump 12 (usually another pump) to a filter 40 through which the blood flows for separation, washing, and recovering of healthy, cleansed blood cells. A blood reservoir (not shown) contains a supply of blood from a patient rather than during an operation. A reservoir for wash solution 20 is connected to pump 18 by flow line 22 which continues to deliver the saline wash solution to wash solution inlet 52 of filter 40. Pump 12 acts to create a steady flow of blood under pressure through line 6 to blood inlet 52 of filter 40. Pump 18 is operated by a controller 24.

The wash solution is preferably an aqueous saline wash solution of a composition and concentration compatible with blood, although any useful wash solution may be utilized Flow lines are made from flexible materials and are well-known to be compatible with blood and may be supplied by any sufficient source. Roller pumps are preferred so that the pump will not be exposed to the blood and further hemolysis will be minimized. Since the pump console is not exposed to the blood, it will remain sterile and reusable. The flow lines must be made of a biocompatible material. Blood reservoirs, when used, are well-known in the prior art and may contain suitable known means for defoaming the blood following suction of the operative area.

Blood filtered to remove gross particles is transmitted to the filter 40 through flow line 6 entering through port 52. The blood flows across membranes in filter 40, as described later, to exit the filter 40 through outlet 82 through flow line 26 to collection bag 28 or directly to patient 4. Pressures must be high enough to result in a high speed flow through the filter 40 and yet low enough to avoid increased hemolysis. Pressures at inlet 52 in the range of from about 10 mmHg to about 450 mmHg are satisfactory depending upon the operating parameter of the membrane selected. The presently preferred pressure range being from about 20 to about 40 mmHg. The pressure drop across the membrane causes fluids to flow through filter 40 is monitored by transmembrane pressure sensor 25, which conveys the information to the microprocessor 16. The lower pressure at the outlet 82 (about 5 mmHg) of the filter 40 and at the filtrate discharge port 70 (about 5 mmHg) allows, respectively, for the flow and removal of healthy blood cells and for the flow and removal filtrate. The washing solution is pumped into inlet 57 at about 55 mmHg, a pressure sufficient to cause an injection of that wash solution into a lower pressure flow of healthy red blood cells. The foregoing pressures are representative and offered for guidance. The pressures are readily fixed by the skilled artisan using the discussions herein.

As is known in the art, such a filter includes a membrane or membranes with pores sufficiently small to prevent the passage of the suspended red blood cells which are to be filtered out of the liquid medium. In the filter of the invention, the ultrafiltration process takes place within a closed housing. Filter 40 may be formed or molded from any suitable biocompatible filter material. In the preferred embodiment the filter 40 is made of plastic so that it may be economically discarded after use. One embodiment of the filter of this invention has rotatably mounted disc which rotates in response to a drive motor 38 connected to microprocessor 16.

Figure 2:
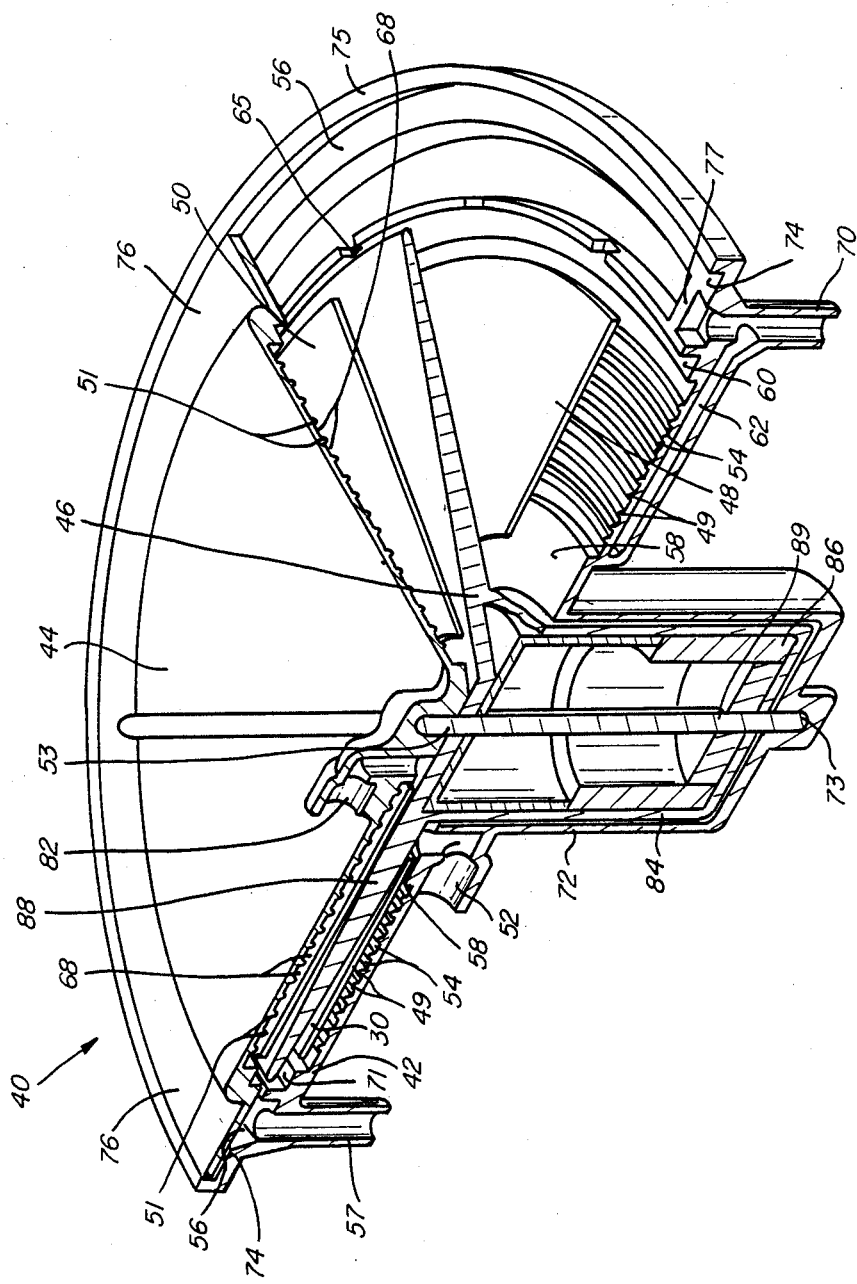
FIG. 2 is a perspective view of a preferred embodiment of a filter of the present invention partially in cross-section with portions of the elements of the filter removed for clarity and detail.
Figure 3:
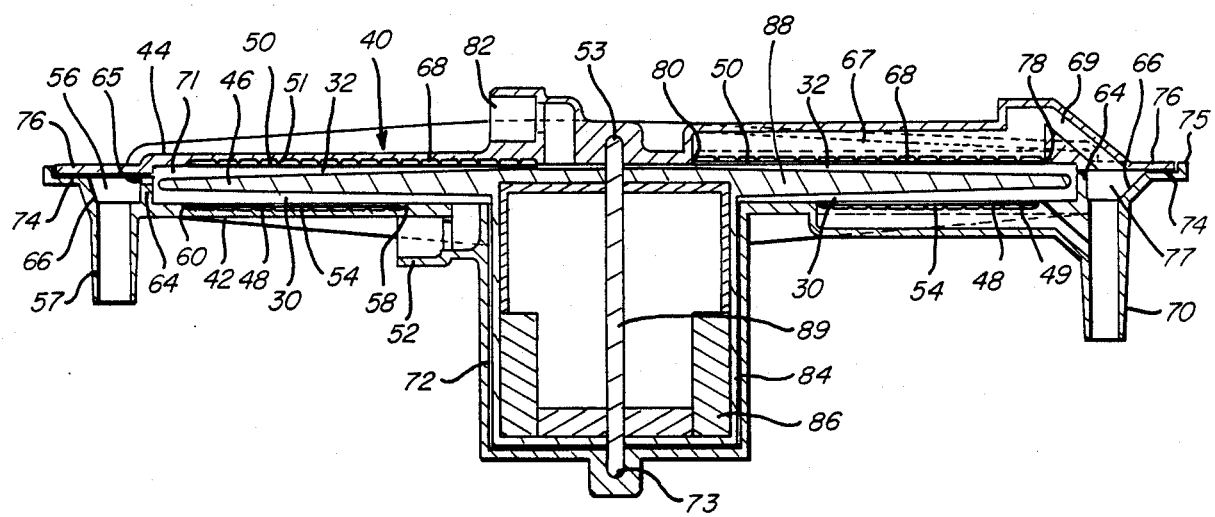
FIG. 3 is a sectional elevation of the embodiment of FIG. 2 showing the filtration collection passages of the two plates.

Filter 40 shown in FIGS. 2 and 3 generally comprises a first plate 42, usually of molded plastic, such as for example polypropylene, polyethylene, polyvinyl acetate, and the like, which is sealingly attached to a second plate 44 by, for example, adhesive, solvent bond, heat seal or sonic weld means to form an interior chamber closed to the outside except as described herein. Enclosed within the plates 42 and 44 is a partition 46 dividing the chamber into three zones as described later in this embodiment, shown and referred to as a disc, and two flat, annular, donut-shaped membranes 48 and 50; membrane 48 being attached to the first plate 42 and membrane 50 being attached to the second plate 44 in a manner known to those skilled in the art to be adhesive, heat or sonic welding, solvent bonding, or the like.

Membrane filter 48 is positioned in the divided interior chamber to create a first filtration zone 30 and has pore size ranging from about 0.02 to about 1.2 microns, preferably from about 0.2 to about 0.5 microns, and is used to separate blood fluids and anticoagulant when applicable, from the larger diameter healthy red blood cells. Membrane filter 50 is positioned in the divided interior chamber to create a second filtration zone 32 and has pore size in the same range as above and separates washing solution and residual blood fluids from healthy red blood cells prior to return to the patient. The membranes 48 and 50 may be composed of any sufficient biocompatible material such as cellophane, cuprophane, polysulphane, expanded polytetrafluoroethylene, a ceramic material, a porous plastic material or a beaded glass material. The membranes 48 and 50 are disposable and inexpensive and are normally used for only a single patient. Membranes 48 and 50 are supported, respectively, by a series of circumferential ribs 49 and 51, which are interrupted along a common radius to form filtrate channels in the discharge chambers (described later). First plate 42, generally includes inlet port 52 which is in fluid communication with first filtration zone 30. When filter 40 is disc shaped, inlet port 52 is located proximate the center of first plate 42. First discharge chamber 54 is a recessed annular surface with inner shoulder 58 lying outside the region of the inlet port 52 and an outer shoulder 60 extending nearly to the outer circumference of disc 46 which carries the edges of membrane 48. The surface of discharge chamber 54 includes first annular ribs 49 which are concentric and formed for the support of membrane 48. Discharge chamber 54 includes discharge channel 62 through a radial gap in ribs 49 which is enlarged and fluidly connected to discharge port 70. The outer annular flange 74 of first plate 42 provides a support area for flange 76 preferably bounded by lip 75 for the attachment of the second plate 44 to the first plate 42 and to provide a boundary to one side of manifold 56 when filter 40 is assembled. First plate 42 and second plate 44 can be attached in any of the usual known methods, i.e., sonic or heat sealing, adhesives, solvent welding, or the like.

Substantially flat membrane 48 is attached to first plate 42 to form a porous filtration layer between the first filtration zone 30 of filter 40 and the discharge chamber 54 which communicates with outlet 70. The inner and outer radii of membrane 48 are sufficient to allow membrane filter 48 to cover the entrance to discharge chamber 54 while not encroaching upon inlet port 52 and injection slots 65. Housing 72 is formed to receive hub 84 of rotating disc 46 and for connection to magnetic rotational driving means 86 in form of magnets as known in the art. Bearing 73 is located in the center of housing 72 to support rotating disc 46.

Injection manifold 56 is located around the outer circumference of filter 40 and is molded into first plate 42 and is bounded inner wall 64 and bounded on the opposite side by outer wall 66. Manifold 56 includes wash solution inlet 57 for receiving washing solution via flow line 22 from washing solution reservoir 20. The circumferential manifold 56 is interrupted in the vicinity of outlet 70 by two barriers 77 (only one shown) placed on either side of outlets, which radially extend across manifold 56 to form a channel for filtrate exiting filter 40 from discharge chamber 54 through discharge channel 62 and port 70. When filter 40 is assembled, outer wall 66 is in contact with second plate 44 at flange 76 fitting with lip 75. Inner wall 64 also contacts second plate 44 but has a plurality of injection slots 65 spaced about the inner wall 64 which allow washing solution to be injected into the washing zone 71 of filter 40.

Second discharge chamber 68 is a sunken annular surface in second plate 44 with an outer shoulder 78 extending nearly to the outer circumference of rotating disc 46 and an inner shoulder 80 located outside outlet port 82 upon which membrane 80 is attached and carried. Bearing 53 is located in the center of plate 44 to support a rotatably mounted disc 46. The surface of discharge chamber 68 includes annular ribs 51 (FIG. 2) which are concentric and formed for the support of membrane 50. Discharge chamber 68 includes second discharge channel 67 which is fluidly connected to discharge port 70 through channel 69. Outlet port 82 is shown elbowed from bearing 53 at an angle for convenient attachment of flow line 26.

Substantially flat membrane 50 is attached to second plate 44 as stated above to form a porous filtration medium between the second filtration zone 32 of filter 40 and the second discharge chamber 68. The inner and outer radii of membrane 50 are sufficient to allow membrane 50 to cover the entrance to discharge chamber 68 and rest on shoulders 78 and 80 while not encroaching upon injection chamber inner wall 64 and outlet 82. Discharge chamber 68 is enlarged to form a discharge channel 67 formed by radian interruption of ribs 51 to ease the collection of filtrate through membrane 50 for discharge through outlet 82.

Membranes 48 and 50 are attached to first plate 42 and second plate 44, respectively, on the described shoulders by adhesive, solvent bond, heated seal or sonic weld means as is known to those skilled in the art.

Rotating disc 46 includes a hub 84 for connection to magnetic rotational driving means 86, and a disc portion 88 which is enclosed within the interior region of filter 40. Hub 84 is of a sufficient diameter to seal off the interior region of filter 40. The disc 88 may be a uniform thickness. In a preferred embodiment, disc 88 of rotating disc 46 is tapered becoming thinner with distance radially from hub 84, to create an increasing gap (as the diameter of the disc increases) in the first filtration zone between membrane filter 48 and the disc 88. Rotation of the disc causes shearing forces to act against the red blood cells being concentrated as described in European patent application No. 8730236.3 mentioned above. The effects of a shear force upon a filtration process is also described in U.S. Pat. No. 4,191,182 to Popovich. The surface of the rotating disc 46 is smooth to prevent agitation and rough handling of the red blood cells. Rotating disc 46 also contains a central shaft 89 for rotatably positioning rotating disc 46 in bearing 53 of plate 42 and bearing 73 of plate 44.

In the discussion that follows, it should be noted that the flow through filter 40 is the flow of a solution whose composition is changing as it moves through the filter. For instance, the fluid flowing through the interior region of the filter 40 goes through a transition from filtered blood to concentrated red blood cell solution in first filtration zone 30 to washing solution injected-red blood cell solution in washing zone 71 to washed and concentrated red blood cell solution in second filtration zone 32. Splitting off from this flow through the interior region is a flow of blood fluids removed as filtrate through the discharge chambers.

When a partition in the form of a rotating disc 46 is interposed between first plate 42 and second plate 44 in the interior region of filter 40, it is readily seen that the blood must flow, generally, in a radial manner around disc 46 to travel from inlet port 52 to outlet port 82. This flow path will take the solution through a first filtration zone 30 partially bounded by membrane 48 and around the perimeter of the disc 46 in a washing zone 71 and finally through a second filtration zone 32 partially bounded by membrane 50 and disc 46. This provides for washing concentrated red blood cells with a subsequent filtration to remove at least a portion of the wash fluid introduced into the wash zone 71. Previously, washing fluid was introduced into whole blood thus diminishing the effectiveness of the wash.

Blood pumped via flow line 6 enters the inlet 52 of filter 40 at a flow rate of from 100 to about 400 ml./min., preferably from 175 to about 250 ml./min., with a hematocrit of from about 20% to about 35%, preferably from 22% to 27%. As the blood flows in a radial manner through first filtration zone 30 adjacent rotating disc 46 blood fluid and anticoagulant are forced under pressure through membrane 48 into first discharge chamber 54 through first discharge channel 62 and out discharge port 70. By rotating disc 46, a uniform shear force is created upon the cells passing membrane 48 which acts to re-mix the healthy red blood cells remaining in the first filtration zone 30. This prevents clotting and the concentration of red blood cells next to the membrane filter 48 allowing enhanced blood fluid and anticoagulant flow through membrane filter 48. About 90 to about 130 ml./min. of liquid is removed through membrane 48, depending upon the flow rate of the entering fluid.

The once-filtered solution will continue to flow around the perimeter of rotating disc 46 into washing zone 71. Simultaneously, washing solution will be pumped at a flow rate from about 0.75 to 3 times the blood flow rate, preferably about equal to the blood flow rate depending upon concentration desired via flow line 22 through injection port 57 and into manifold 56. Washing solution will be injected through the slots 65 in the inner wall 64 of manifold 56 into washing zone 71 where concentrated red blood cells are washed and diluted. The washing solution should be a plasma replacement solution. A preferred washing solution is a saline aqueous mixture having a salt content of about 0.9%, equivalent to that of normal blood fluids. Rotating disc 46 will enhance the mixing of the washing solution with the flow of the once filtered blood cells in the washing zone 71 to accomplish more complete removal of the anticoagulant.

The washed solution mixture will flow toward discharge chamber 68 and outlet port 82 through second filtration zone 32. Washing solution and residual blood fluids and anticoagulant will infiltrate to discharge chamber 68 through membrane 50 and flow through second discharge channel 67 out discharge port 70. The uniform shear force created by rotating disc 46 upon membrane 50 acts to re-mix the healthy red blood cells remaining in the interior region of filter 40. This prevents clotting and the concentration of red blood cells on the membrane 50 allowing enhanced washing solution and residual blood fluid and anticoagulant flow through membrane 50. About 200 ml./min. of liquid is removed through membrane 50 to leave cleaned, concentrated red blood cells, which will continue to flow toward port 82. About 100 ml./min. of the washed, twice-filtered blood will exit filter 40 via port 82. After exiting, the concentrated red blood cell solution, which is about 50% hematocrit will be transported via flow line 26 to a collection bag 28 or the patient. Bag 28 may be linked directly to the patient or may be used for storage of the concentrated red blood cell solution. Reinfusion or collection bags are well-known and may be made of any suitable biocompatible material.

Discharge port 70 is connected via flow line 90 through pump 92 having controller 94 connected to microprocessor 16, which provides for a pressure drop across membranes 48 and 50 to enhance the filtration of the solution to waste reservoir 96. Waste reservoir 96 may constitute any suitable receptacle.

Figure 4:
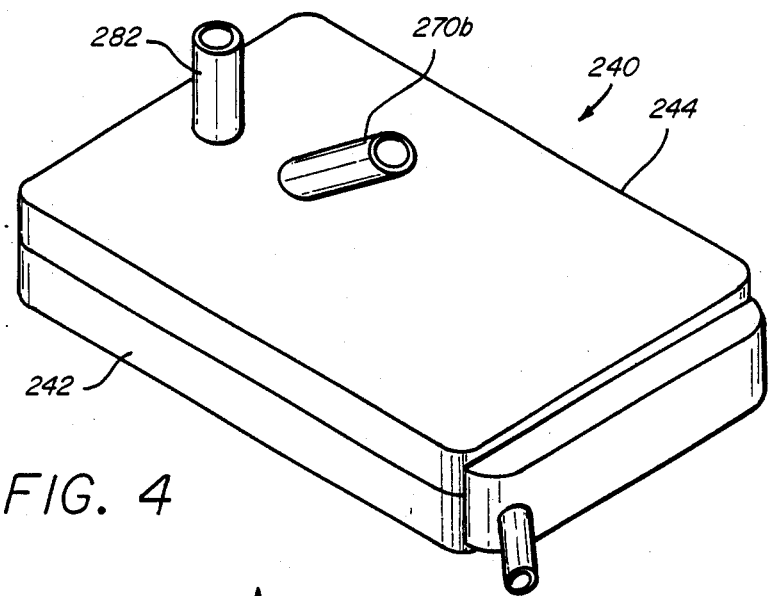
FIG. 4 is a perspective view from the top of a rectangular embodiment of the filter apparatus.
Figure 5:
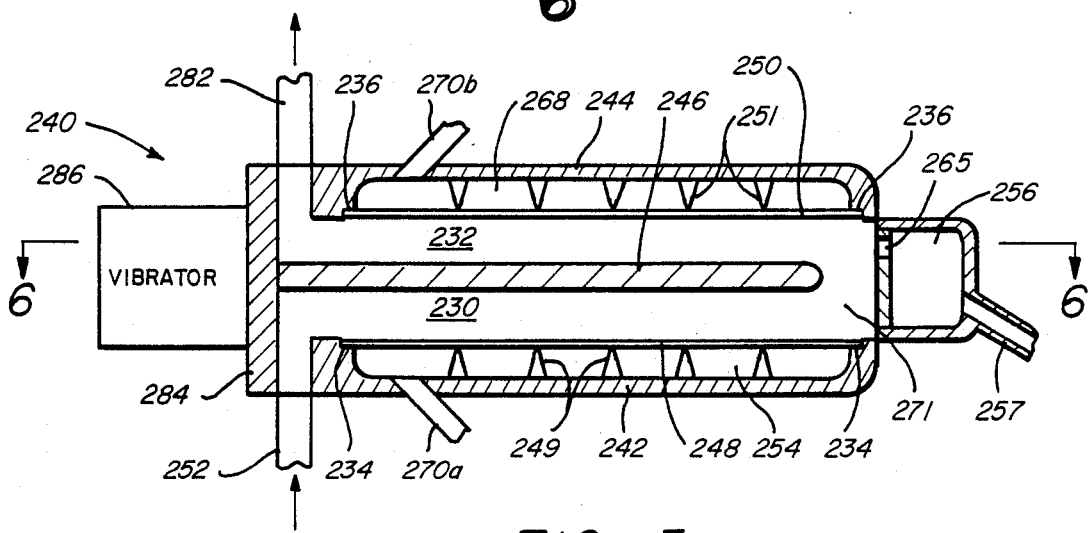
FIG. 5 is a sectioned elevation view of the embodiment shown in FIG. 4.
Figure 6:
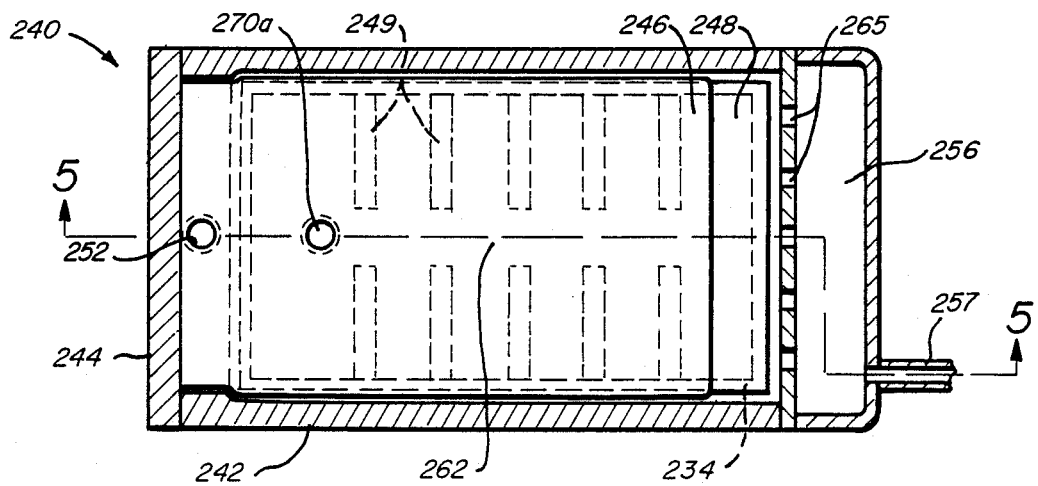
FIG. 6 is a sectioned plan view of the embodiment shown in FIG. 4.

Turning now to FIGS. 4, 5, and 6, where is shown another embodiment of the above-identified invention in a rectangular configuration. Such invention would be described with elements, insofar as possible, following the numbering as set forth with respect to elements in FIGS. 2 and 3, except preceded by the digit "2". In this embodiment a filter 240 is described having a first plate 242 and a second plate 244 drawn together in a manner described as above for such previous embodiment in manners known to those skilled in the art, to form an interior cavity divided by a partition 246 attached to such first plate 242 and such second plate 244 by an end plate 284 having attached thereto a vibrator 286 for imparting energy through plate 284 to partition 246 to stimulate vibration thereof. The interior cavity formed by the joining of first plate 242 and second plate 244 and divided by partition 246 is further separated into a first filtration zone 230 by a porous membrane 248 and a first discharge chamber 254. Such membrane is supported by a shoulder 234 around the perimeter of the first plate 242. Additional support to such membrane 248 is provided by ribs 249 extending transversely across the longitudinal axis of the filter 240 except as interrupted along such longitudinal axis to provide a channel 262 within first discharge chamber 254 for removal of filtrate moving through membrane 248. Such filtrate is removed from discharge chamber 254 through port 270a.

Likewise the interior chamber formed by joining first plate 242 and second 244 forms a second filtration zone 232 by the introduction of membrane 250 resting upon shoulders 236 wherein such membrane is attached in manners described above with the previous embodiment. Said membrane 250 is further supported by ribs 251 extending transversely across said second discharge chamber 268, though interrupted along said longitudinal axis to form a channel 267 to allow filtrate through membrane 250 to be removed from said discharge chamber 268 through port 270b.

Intermediate such filtration zone 230 and second filtration zone 232 is a washing zone 271 which is fed by a saline solution as described above, introduced through slot 265 fed from a manifold 256 receiving its saline solution through an inlet port 257. Thus fed, the saline solution as described in connection with the previous embodiment dilutes the concentrated red blood cells passing through the washing zone 271 to remove additional undesirable materials from the first filtration zone 230 for removal in to the second filtration zone 232.

In the operation of the filter 240 of this embodiment, the whole blood enters the filter 240 through port 252, and thus, into the first filtration zone 230 where the fluid moves past membrane 248 preferably under pressure from input blood pump 12 and the stimulus of the vibrating partition 246 to prevent coagulation or compaction of red blood cells desired where filtrate moves through membrane 248 into the first discharge zone 254 and thence out port 270a. The concentrated red blood cells then proceed from the first filtration zone 230 to the washing zone 271 where it contacts a saline wash solution compatible with the blood and entering through port 265 where the red blood cells are again diluted and moved from the washing zone 271 to the second filtration zone 232 where the fluids are separated from the red blood cells through membrane 250 into the second discharge zone 268 where they accumulate moving through the channel through ribs 251 to port 270b the filtrate exists. The concentrated red blood cells thus passing the membrane 250 exit filter 240 through port 282 for collection, or return to patient 4.

Having thus described in detail two preferred embodiments of the above-identified invention, the following example, more particularly describes and points out the advantages, features, and elements of the invention described herein. This example is offered for purposes of description, exemplification, and amplification of the above-described invention only and should not be construed, considered, or otherwise deemed to be in limitation of such invention. The importance of the initial filtration prior to washing cannot be overemphasized in this day of heinous diseases carried by the blood. Cleaning is more complete with the interim wash step followed by a second filtration.

EXAMPLE

A separator of the type shown in FIGS. 2 and 3 and described in connection therewith, was constructed of acrylic plastic, machined to accept a membrane 6½ inches in outer diameter and ½ inch inner diameter. A first and second membrane were positioned in the first and second distillation zones and sealed to the first and second plates. A rotating disc operating on stimulus from a magnetic motor was installed as described. The disc was 6 inches in diameter having the thickness near the hub of 0.312 inch, and an outer thickness at the perimeter of 0.06 inch, having a uniform taper on both top and bottom. The cell was tested for an extended period of approximately 3 hours continuous to determine filtrate flow rates under given and controlled input flow rates, hematocrit levels and disc rpm.

The filter media was a flat sheet cut to the sizes as set forth above and sealed to the acrylic plates. The filter was a nylon material having 0.8 micro meter pore size (Micron Separations, Inc., Catalog No. N08SPO12.4). The surface area of such filter was 18.5 square inches. The rotor taper would maintain a constant shear rate of 0.83 dynes per square centimeter-rpm.

Figure 7:
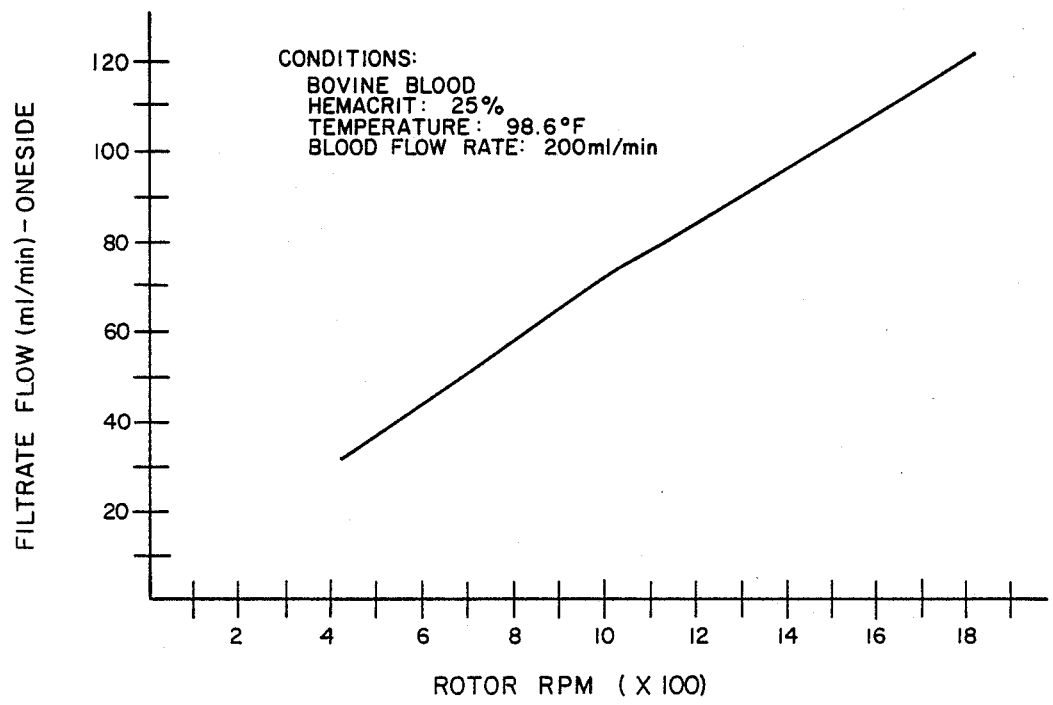
FIG. 7 is a graph showing the relationship between filter rate as a function of rotor speed.

Fresh bovine blood at a hematocrit of 44 (as determined by centrifuge) was combined with an effective amount of anticoagulant (sodium citrate at a 3.8% concentration premixed in distilled water) at the source. This was reduced to a 25 hematocrit using a sterile saline solution and thorough mixing. The blood temperature was maintained at 98.6° F. throughout the test by using a warm water bath. The test results as set forth on FIG. 7 hence show that the filtrate flow rate is directly proportional to rotor or disc rpm. A plasma filtrate of 119 milliliters per minute with an outlet hematocrit concentration of 62 when operating at 1800 rpm, and a blood flow of 200 ml per minute was achieved. High blood flow was obtained and a more pure red blood cell resulted from the interim wash step.

Not withstanding the foregoing specific description of the embodiments of this invention, there is no intention that such invention be limited thereto. Those of ordinary skill in the art would find many obvious variations thereto by reading the foregoing descriptions and example.

What is claimed is:

1. A method for autotransfusion of blood which comprises:
    (a) passing whole blood through a first filtration zone to remove fluid components of blood from blood cells through a filter means to provide concentrated blood cells;
    (b) passing the concentrated blood cells into a wash zone while introducing a wash solution compatible with blood into the wash zone to dilute and wash the blood cells;
    (c) passing the diluted blood cells into a second filtration zone where at least a portion of the wash solution is separated from the blood cells through a second filter means;
    (d) applying shearing forces to red blood cells to prevent build-up of such blood cells on the filter means in said first and second filtration zones; and
    (e) recovering the blood cells.

2. The method of claim 1 wherein the shearing forces are applied simultaneously in the first and second filtration zones by a single rotating disc intermediate the filtration zones.

3. An autotransfusion system to remove particulate refuse and clean blood cells for return to a patient which comprises:
    means for salvaging a blood mixture from a patient;
    a filter assembly in fluid communication with said salvaging means, said filter assembly having a first membrane and defining a first filtration zone, having a second membrane and defining a second filtration zone, where said first and second membranes are selected to allow the forced infiltration of fluids in the blood mixture, under pressure into a discharge chamber, while passing the red blood cells within the filtration zones;
    means for injecting after said first filtration zone a pressurized flow of a washing solution into said red blood cells which defines a washing zone;
    means for pressurizing the filtration zones of said filter assembly wherein at least a portion of the fluids in the blood are forced through said membranes;
    a partition which partially bounds and separates said filtration zones and sequentially channels the flow of filtered blood through the first filtration zone, the washing zone, and the second filtration zone,
    means in fluid communication with filtration zones for removing the filtrate from said filter assembly; and
    means in fluids communication with the second filtration zone for returning clean red blood cells to the patient.

4. The autotransfusion system of claim 3 wherein the partition is a disc.

5. The autotransfusion system of claim 4 which further comprises:
    a means for rotatably mounting said disc; and
    means connected to said disc for rotating said disc whereby the rotation of said disc creates shearing forces upon the red blood cells and prevents clotting and the build-up of red blood cells on said first and second membranes.

6. The autotransfusion system of claim 4 wherein the disc is tapered whereby said shearing forces are exerted equally along the surface of the membranes.

7. A filter assembly, comprising:
    a first plate which includes:
        an inlet port for receiving blood;

a first membrane adjacent said inlet port, said membrane selected to allow the infiltration of refuse and prevent the infiltration of cells as the filtered blood flows across said first membrane; and a first discharge chamber adjacent said first membrane for receiving the filtrate;

a second plate attached on the perimeter to said first plate to create an interior space which includes:

an outlet port for the removal of the filtered and washed cells;

a second membrane selected to allow the infiltration of washing solution and, residual blood fluids and prevent the infiltration of cells flowing across said second membrane;

a second discharge chamber adjacent said second membrane for receiving the filtrate;

a partition dividing said interior space between said plates creating a first filtration zone and a second filtration zone and a washing zone intermediate the filtration zones proximate the edge of said partition; and an injection manifold about the perimeter of said plates external said membranes which receives pressurized washing solution for injection into a washing zone for filtered cells, said manifold having a plurality of injection ports to provide fluid communication between said injection manifold and washing zone for receiving washing solution.

8. The filter as described in claim 7 wherein the plates and partition are discs oriented about a common central axis.

9. The filter as described in claim 8 wherein the partition disc is rotatably mounted about a hub and collar supports a rotational driving means and with a hub rotatably positioned between said first and said second plates wherein the filtered blood solution must travel around the perimeter of said disc in a radial manner to flow from said inlet port to said outlet port.

10. The filter assembly of claim 7 which further comprises: means in fluid communication with said first and second discharge chambers whereby filtrate is removed from the filter assembly.

11. A filter, comprising:

a disc-shaped body having a saucer shaped top and bottom, an inlet port in said bottom an outlet port in said top, an annular cavity in said bottom and top, each covered by a membrane and defining a first and second filtration zone, respectively, to receive filtrate passing through said membranes and a washing solution injection port located on said body after the first filtration zone; and a rotatable disc interposed within said disc-shaped body separating the first and second filtration zones.

12. A filter according to claim 11 wherein said inlet port is centrally located.

13. A filter according to claim 11 wherein said washing solution injection port is located on the perimeter of said body.

14. An apparatus for autotransfusion from a surgical patient, comprising:

means for continuously receiving a mixture of blood cells, liquid, and particulate refuse from a patient;

a filtration unit capable of removing at least a portion of the liquid from the mixture comprising:

(i) a disc-shaped body having a saucer shaped top and bottom, an inlet port in said bottom and an outlet port in said top, an annular cavity in said bottom and top, each covered by a membrane and defining a first and second filtration zone, respectively, to receive filtrate passing through said membranes and an injection port for washing solution located on said body after the first filtration zone; and (ii) a rotatable disc interposed within said disc-shaped body separating the first and second filtration zones; and (iii) means for removing the concentrated red blood cells through the outlet port from said filtration unit for return to the patient.

15. An apparatus as defined in claim 14 wherein said rotatable disc is tapered.

16. The autotransfusion system of claim 3 where said salvaging means includes a filter capable of removing at least a portion of the particulate refuse.

* * * * *